United States Patent [19]
Trifonov et al.

[11] Patent Number: 6,015,878
[45] Date of Patent: Jan. 18, 2000

[54] ANTITUMOR AGENTS ISOLATED FROM INTESTINAL MUCOSA, A METHOD FOR THEIR ISOLATION AND THEIR APPLICATION

[75] Inventors: Borislav Borisov Trifonov, Plovdiv; Jeorge Konstantinov Roussev, Sofia; Nikola Atanassov Boshev, Polvdiv, all of Bulgaria

[73] Assignee: Alexandrov, Christo Alexandrov, Plovdiv, Bulgaria

[21] Appl. No.: 08/849,821

[22] PCT Filed: Mar. 4, 1996

[86] PCT No.: PCT/BG96/00003

§ 371 Date: Oct. 2, 1997

§ 102(e) Date: Oct. 2, 1997

[87] PCT Pub. No.: WO97/15590

PCT Pub. Date: May 1, 1997

[30] Foreign Application Priority Data

Oct. 20, 1995 [BG] Bulgaria .................................. 1000075

[51] Int. Cl.[7] .............................. A61K 38/00; C07K 7/00
[52] U.S. Cl. .............................. 530/329; 530/344; 514/2; 514/8; 514/17; 514/21; 424/550; 424/551
[58] Field of Search ..................................... 424/550, 551; 530/329, 344; 514/2, 8, 17, 21

[56] References Cited

FOREIGN PATENT DOCUMENTS 0049927 3/1992 Bulgaria .

OTHER PUBLICATIONS

Copy of Search Report from PCT/BG96/00003 New Enterocytic Peptides with Morphogenic Effect, Folia Medica, 37(4A): 30 (1995).

Biological Effects of a Novel Intestinal Peptide–Inhibiting Enterocytogenin on Cultured 3T3 Mouse Fibroblast and L51784 Mouse Lymphoma Cells, Regulatory Peptides, 51(2): 111–119 (1994).

Altered Bioelectrical and Mechanical Activites of Rat Gastric Smooth Muscle Preparations by Inhibiting Enterocytogenin, 61(2): 119–123 (1996).

English Translation of BG 49927, Mar. 30, 1992.

*Primary Examiner*—Bennett Celsa
*Attorney, Agent, or Firm*—Fitch, Even, Tabin & Flannery

[57] ABSTRACT

This invention provides a method for isolating antitumor agents, inhibiting enterocytogenins, from pig intestinal mucosa. It further provides the antitumor agents, which are nucleopeptides. Additionally the invention provides methods for suppressing the growth of certain tumor cells comprising administering an inhibiting enterocytogenin to tumor cells.

2 Claims, 3 Drawing Sheets

ANTITUMOR AGENTS ISOLATED FROM INTESTINAL MUCOSA, A METHOD FOR THEIR ISOLATION AND THEIR APPLICATION

BACKGROUND OF THE INVENTION

This invention relates to a method for isolation of two agents with cytostatic action from pig intestinal mucosa which were shown experimentally to exert an inhibitory effect on cell pro-liferation.

BRIEF DESCRIPTION OF PRIOR ART

Our previous studies [1] have shown that cell differentiation causes the emergence of specific morphogenic stimulators and inhibitors generally referred to as ontogenins; in particular, stimulating (SEG) and inhibiting (IEG) enterocytogenins were isolated from the physiologically regenerating mucosa cells [2]. In later studies we have reported data indicating that there are substances of chalonic type in the colonic mucosa which inhibit specifically the cell proliferation in the colon [3].

SUMMARY OF THE INVENTION

The objects of the present invention are:

1. To specify, under industrial conditions, the method for producing the two inhibiting enterocytogenins ($IEG_1$ and $IEG_2$).

2. To identify these enterocytogenins chemically.

3. To test in experimental animals the effect of $IEG_1$ and $IEG_2$ on the morphogenic and biosynthetic processes.

4. To test in vitro $IEG_1$ in normal and malignant cellular cultures and study its effect on transplantable experimental tumors in vitro-in vivo and only in vivo.

Figure 1:
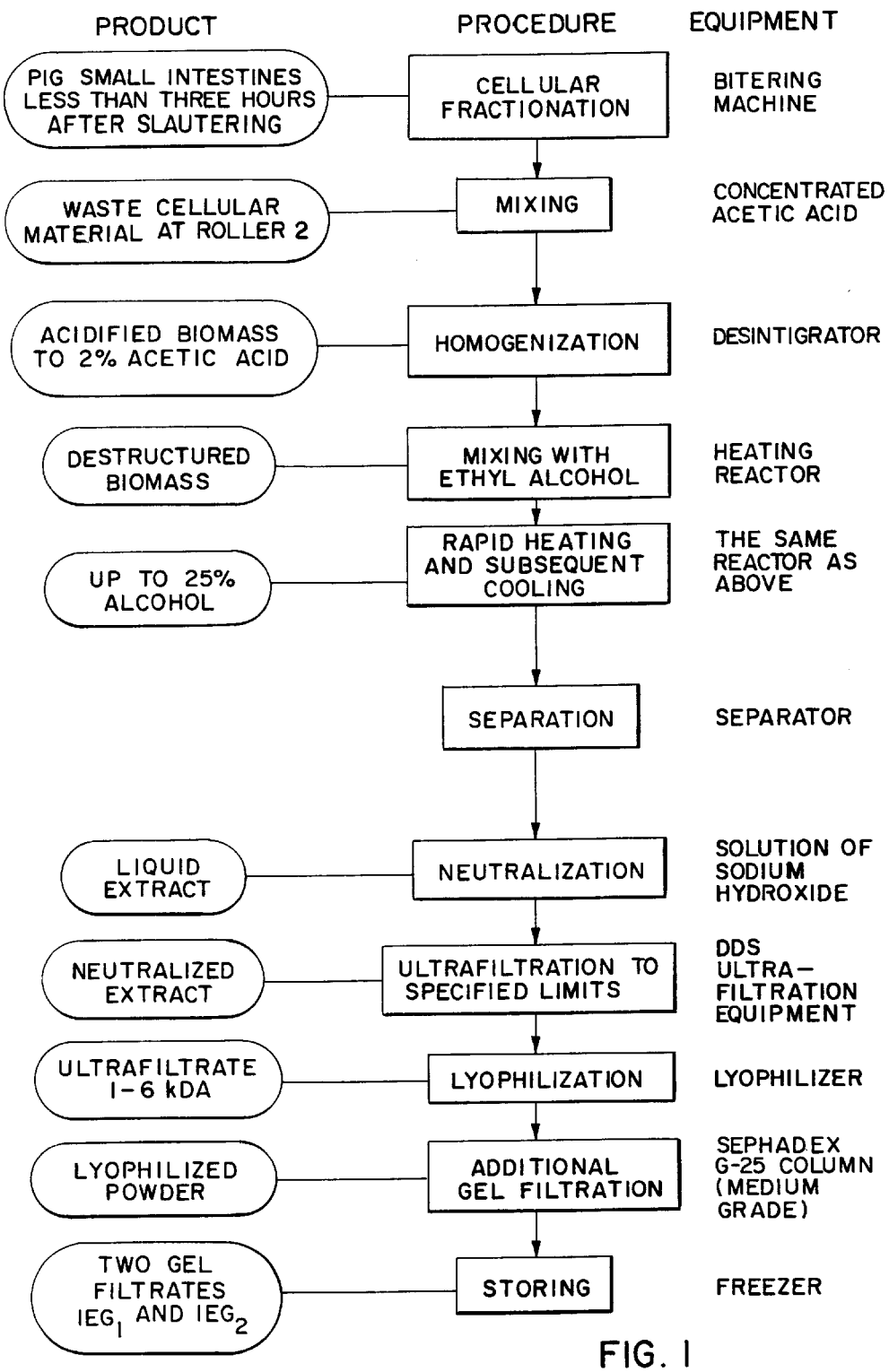
FIG. 1. shows a flow chart for the isolation of $IEG_1$ and $IEG_2$.
Figure 3:
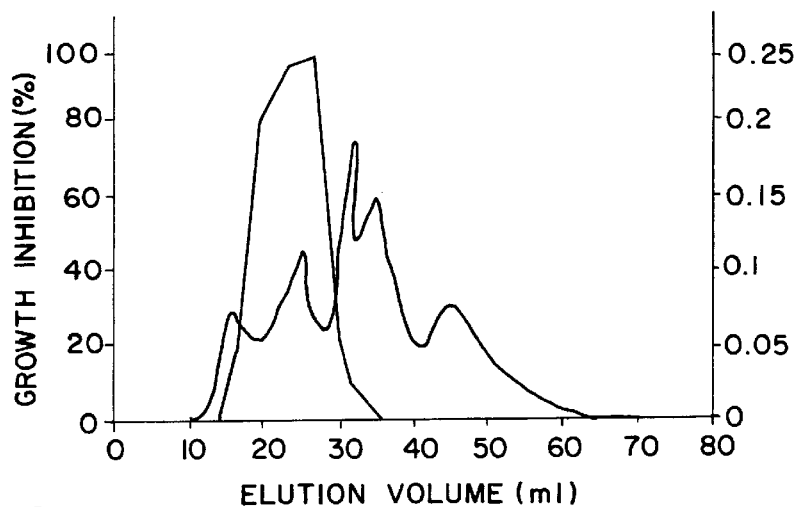
FIG. 3 illustrates a gel filtration of $IEG_1$ and the effect of various fractions on tumor growth.

The first object is achieved by providing a method for isolating inhibiting enterocytogenins from pig intestinal mucosa as described in FIG. 1. The production scheme under industrial conditions includes: 1. Fractionation of waste cellular mass from intestinal mucosa to a specific cellular type; 2. Extraction of high molecular polymers with 2% acetic acid and subsequent precipitation by alcohol; 3. Separation and after filtration the light fraction is ultrafiltered through a DDS filter (10 kDa); 4. Lyophilization of the ultrafiltrate and subsequent separation through molecular sifts.

Figure 2A:
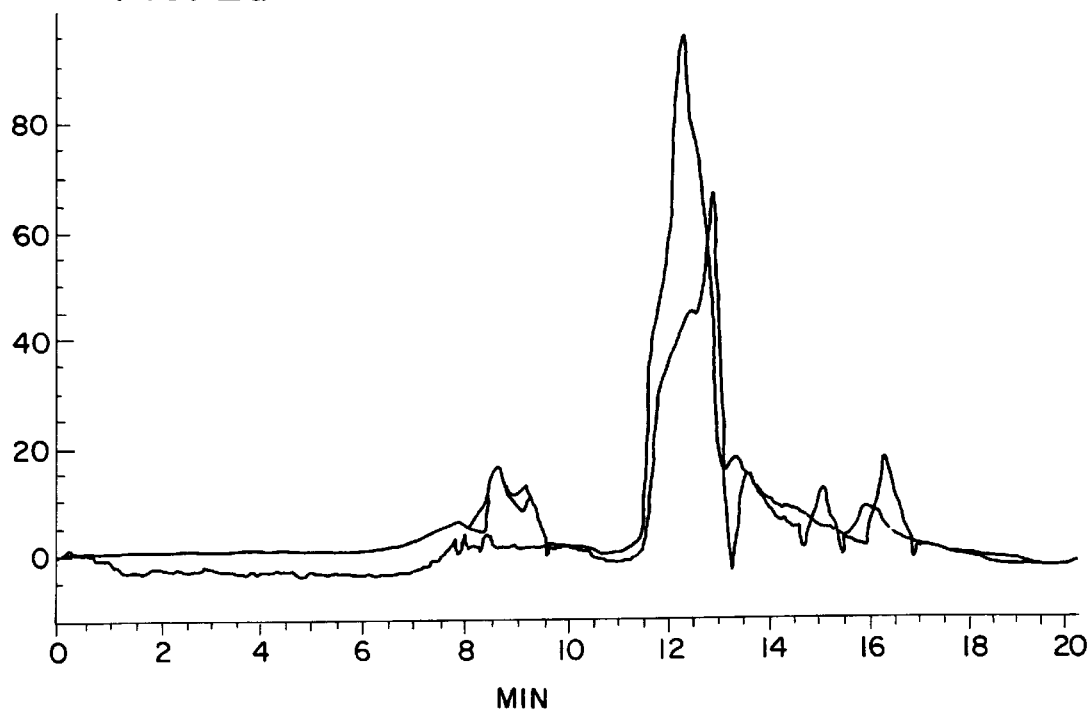
FIG. 2a illustrates an HPLC-purification of $IEG_1$.

The second object is achieved by obtaining highly purified preparation under laboratory conditions using FPLC and HPLC methods as described for $IEG_1$ in FIG. 2a. The conducted quality chemical and spectral analysis identifies $IEG_1$ and $IEG_2$ as nucleopeptides; the amino acid content was determined by an amino acid analyser.

DETAILED DESCRIPTION OF PREFERRED EMBODIMENTS

Laboratory experiments were carried out to accomplish the third object concerning the effect of preparations on biosynthetic processes which was assessed by the incorporation of $H^3$-thymidine (DNA-synthesis) and $C^{14}$-uridine (RNA synthesis) in various regions of the intestines of the mice tested. The preparation's morphogenic effect was assessed by the enterocytic cellularity and DNA concentration in the same regions.

The fourth object is accomplished by studying the effect of $IEG_1$ on cellular cultures of 6 normal and 7 malignant cell lines in vitro, on a transplantable solid tumor in vitro-in vivo and on one tumor only in vivo.

The invention will be described by way of the following examples:

EXAMPLE 1

Object 1 (FIG. 1)

The cellular mass removed at casing stripping roller No 2 on a Biterling machine in the casing cleaning wards of slaughter houses is collected and concentrated acetic acid is added, at constant stirring, to achieve a final concentration of 2% acetic acid relative to the whole mass. The mass so prepared is subjected to cellular destruction on a disintegrator followed by precipitation of the polymers heated in a reactor with 3 volumes of 96% ethyl alcohol. The light fraction is separated in a separator and then filtered; its pH is adjusted to pH 6.5–7.0 and ultrafiltered through DDS filter to 6000–1000 Da. The collected filtrate is lyophilized and can be stored at a temperature of −10° C. retaining its biologic activity for 5 years. When working with it 0.1 g of the lyophisate is dissolved in 0.5 ml $H_2O$ and purified additionally by gel-filtration on SEPHADEX G-25 (medium grade).

EXAMPLE 1

Figure 2B:
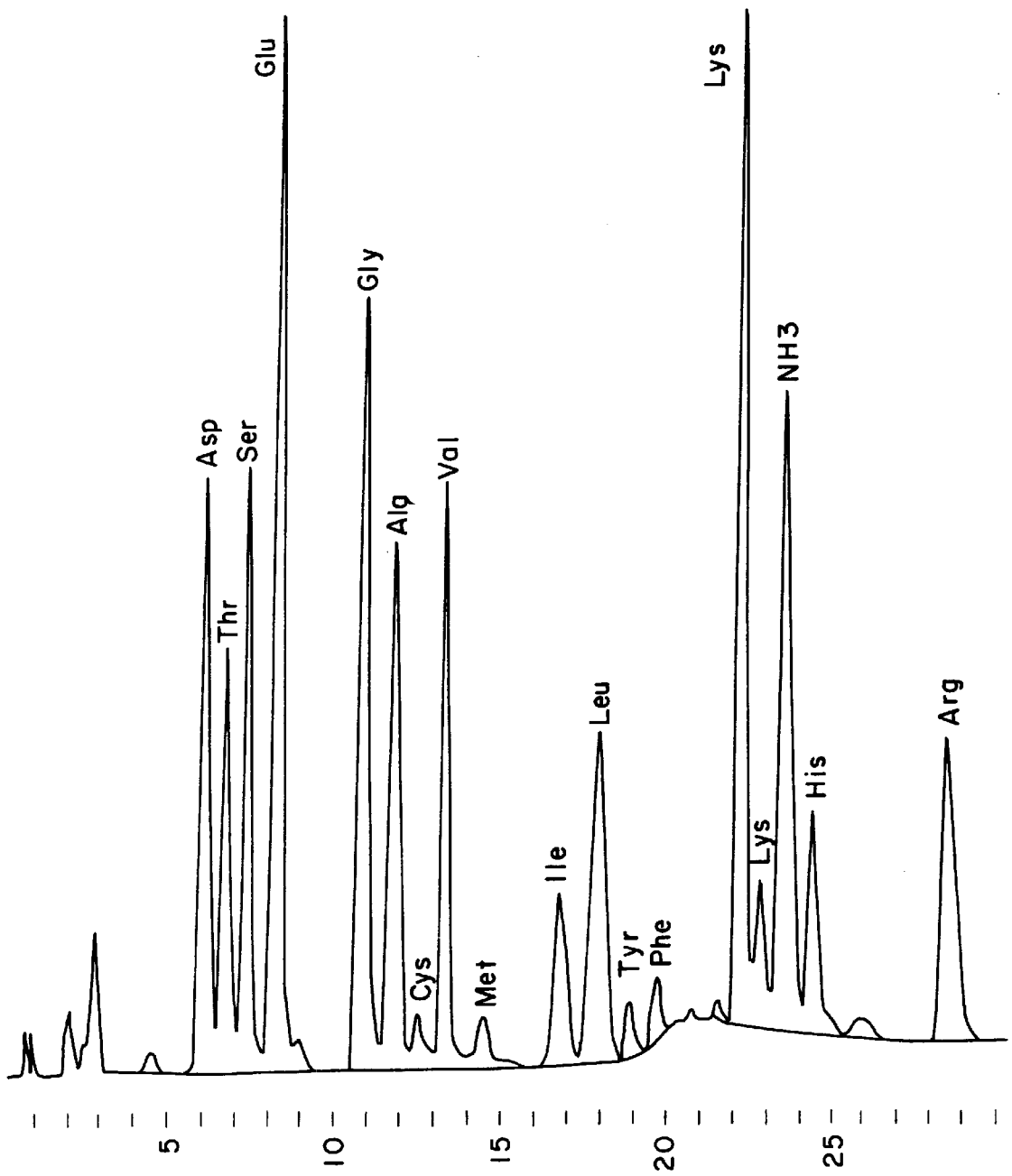
FIG. 2b shows the amino acid content of $IEG_1$.

Object 2 (FIGS. 2a and 2b)

The molecular weight of the bioactive fractions purified in Object 1 was determined on a silicagel SORBAX column using HPLC apparatus (FIG. 2a) $IEG_1$ was found to have molecular weight of 4450±180 Da, and $IEG_2$–950±120 Da. UV spectral analysis revealed two absorption maxima: for $IEG_1$ at 220 nm and 248 nm and for $IEG_2$ at 220 nm and 245 nm. Presence of guanosine in both IEGs identified them as having nucleopeptide nature. The amino acid analyser (FIG. 2b) showed that $IEG_1$ contained glutamine (13.33%) followed by lysine (10.95%), serine, threonine, asparagine, glycine, alanine, valine, isoleucine, leucine, histidine, and arginine. Cyctine, methionine, tyrosine and phenylalanine were present probably in a mixed state (<1.5%, Table 1). $IEG_2$ is a hexapeptide with the following amino acid sequence: Arg-Arg-Asp-Asp-His-Arg-$NH_2$. SEQ. ID. NO. 1 Computer analysis of the amino acid content of $IEG_1$

| No. | NAME | RT | HEIGHT | AREA | n mol | % | ng | RATIO |
|---|---|---|---|---|---|---|---|---|
| 1 |  | 4.32 | 1438 | 31566 | 0.031 |  | 0.0 | 0.0 |
| 2 | Asp | 5.86 | 36209 | 645265 | 2.414 | 6.94 | 321.4 | 100.6 |
| 3 | Thr | 6.53 | 25623 | 468376 | 1.627 | 4.68 | 193.8 | 100.5 |
| 4 | Ser | 7.14 | 36698 | 624028 | 2.111 | 6.07 | 221.8 | 99.1 |
| 5 | Glu | 8.02 | 65067 | 1186968 | 4.633 | 13.32 | 681.5 | 99.1 |
| 6 |  | 8.74 | 1958 | 54995 | 0.054 |  | 0.0 | 0.0 |

-continued

| No. | NAME | RT | HEIGHT | AREA | n mol | % | ng | RATIO |
|---|---|---|---|---|---|---|---|---|
| 7 | Gly | 10.61 | 46608 | 916917 | 3.274 | 9.42 | 245.8 | 98.4 |
| 8 | Ala | 11.57 | 32003 | 789776 | 3.089 | 8.89 | 275.2 | 100.8 |
| 9 | Cys | 12.29 | 3368 | 90129 | 0.319 | 0.92 | 76.8 | 216.6 |
| 10 | Val | 13.09 | 35429 | 562107 | 1.989 | 5.72 | 233.1 | 96.0 |
| 11 | Met | 14.32 | 3148 | 111300 | 0.525 | 1.51 | 78.3 | 163.7 |
| 12 | Ile | 16.61 | 10418 | 287121 | 1.306 | 3.76 | 171.4 | 99.1 |
| 13 | Leu | 17.73 | 20034 | 578395 | 2.683 | 7.72 | 352.7 | 100.7 |
| 14 | Tyr | 18.64 | 3282 | 58156 | 0.447 | 1.29 | 81.1 | 95.1 |
| 15 | Phe | 19.49 | 3879 | 68355 | 0.308 | 0.89 | 50.9 | 86.5 |
| 16 |  | 21.25 | 1137 | 12883 | 0.012 |  | 0.0 | 0.0 |
| 17 | Lys | 21.84 | 77180 | 1189568 | 3.805 | 10.95 | 556.3 | 99.7 |
| 18 |  | 22.48 | 8631 | 174505 | 0.174 |  | 0.0 | 0.0 |
| 19 | NH3 | 23.17 | 38740 | 975264 | 0.528 |  | 42.9 | 101.0 |
| 20 | His | 24.13 | 13573 | 304124 | 0.982 | 2.82 | 152.5 | 105.1 |
| 21 |  | 25.62 | 1142 | 48214 | 0.048 |  | 0.0 | 0.0 |
| 22 | Arg | 28.34 | 18289 | 512259 | 2.077 | 5.98 | 361.8 | 100.6 |
| 23 | Pro |  |  |  | 3.168 | 9.12 |  |  |
| Total |  |  | 483843 | 9690271 | 35.604 |  | 4097.3 |  |

EXAMPLE 1

Object 3 (Table 2)

Each fraction obtained in purifying IEG (see Object 1) was tested on mice. 3 mg of the peptide content of the fraction was administered intraperitoneally simultaneously with the testing reagent (isotope); the animals were then killed and investigated 7 hours afterwards. Treatment with $IEG_1$ for 7 hours resulted in reducing the number of erythrocytes by 24% on the average, and with $IEG_2$ —by 20%. Both IEGs have a suppressive effect on DNA synthesis especially in the lower regions of intestines: $IEG_1$ by 45%, $IEG_2$ —by 48%. In previous studies [4] we proved that $IEG_1$ elevates the cytosol level of $Ca^{2+}$ in smooth muscle cells by using the intracellular cellular $Ca^{2+}$ depots. In this way it switches on the chain of molecular mechanisms by which it acts on the smooth muscle motility.

TABLE 2

Effect of $IEG_1$ and $IEG_2$ on the biosynthetic and morphologic processes in the intestines
(7 hours after treatment of mice with $IEF_1$ and $IEG_2$)
(The data are presented in percentages in comparison with control animals not treated with IEGs)

| IEG | Section of the intestines | Incorporation | | DNA concentration | Cellularity |
|---|---|---|---|---|---|
|  |  | $H^3$-thymidine | $C^{14}$-uridine |  |  |
| $IEG_1$ | Duodenum | 74 | 75 | 66 | 82 |
|  | Jejunum | 94 | 67 | 84 | 95 |
|  | Ileum | 57 | 68 | 69 | 81 |
|  | Middle section of the intestines | 52 | 62 | 58 | 76 |
| $IEG_2$ | Duodenum | 77 | 78 | 68 | 88 |
|  | Jejunum | 88 | 78 | 97 | 75 |
|  | Ileum | 55 | 74 | 77 | 85 |
|  | Middle section of the intestines | 48 | 74 | 62 | 83 |

EXAMPLE 1

Object 4 (Table 3)

$IEG_1$ has a strong antitumor effect on malignant cellular cultures. It also has a well pronounced cytotoxic effect on Lewis lung carcinoma cells (LLCa) both in vitro and in vivo in mice line C57BI which was proved by means of the combined method in vitro-in vivo and so-called bioassay for determination of surviving tumour cellular fraction of LLCa. There is a marked concentration-effect dependence. The inhibition index of tumour growth (IITG) of the subcutaneous form of LLCa is 88.2% (at a concentration of $IEG_1$ 1050 μg/ml). The observed pathomorphologic changes correlate with the dose-dependent effect of $IEG_1$. $IEG_1$ exerts in vivo an effect on the development of an experimental transplantable solid tumour in golden Syrian hamsters (flat cellular carcinoma IC-Sofia-line 7). IITG in this experiment was 60.5% (therapeutic dose of $IEG_1$ in the range of $4 \times 10^{-3}$ g/kg to $3.5 \times 10^{-4}$ g/kg. The inhibition of DNA synthesis in the tumour was −48%; the mitosis were reduced to 21.9% in comparison with the same parameters in the tumours of non-treated animals ($P < 0.01$).

TABLE 3

Effect of IEG$_1$ on cellular cultures

| Cell line | Origin | | IC$_{50}$(µg/ml) | |
|---|---|---|---|---|
| | | | NR-test | KBP-test |
| NORMAL CELL LINES | | | | |
| 3T3 | fibroblasts | mice | 123.9 | 187.5 |
| FL | amnionic* | human | 223.2 | 264.4 |
| BHK | kidney* | golden Syrian hamster | >300 | >300 |
| CHO | ovarium* | hamster | 213.2 | 256.4 |
| MDC | kidney | dogs | 192.6 | 247.4 |
| Vero | kidney | African green monkey | 156.7 | 197.3 |
| MALIGNANT CELL LINES | | | | |
| L 5178 | lymphoma | mice | 192.8 | 212.6 |
| Hep 2 | carcinoma of the larynx | human | 290.4 | 300.0 |
| Hela | epitheloid carcinoma in the uterus | human | 291.5 | 268.5 |
| RD | embryonal rabdomyosarcoma | human | 196.15 | 276.3 |
| Sp 2 | myeloma** | mice | 206.2 | 226.2 |
| Ag8 | myeloma** | mice | 1998.9 | 234.8 |
| METH | myeloma** | mice | 212.3 | 246.5 |

**suspension cell lines
*continuous lines

References

1. Roussev GK. Programmed manipulation of embryonic development. Ontogenins. Sofia, Nauka y Izkustvo, 1974, 1–301.

2. Roussev GK, Trifonov B, Petrov M, Boshev H. A method for isolation of substances with morphogenic activity. Invention patent 37396 MPK-A 61K35/38, Vol 6, Jun. 14, 1985, 1–6.

3. Skraastad O, Reichelt KI. An endogenous colon mitosis inhibitor and dietary calcium inhibit the increased colonic cells proliferation induced by cholic acid. J Gastroent 23 (1988), 801–807.

4. Trifonov B, Kristev A, Zaprianov G, Lukanov J, Kostadinova I. Effects of a novel intestinal peptide (enterogenin) on the contractile and bioelectric activity of intestinal smooth muscle from the rat and the guinea-pig. J Gastrointest Motil 4, (1992), 193–199.

What we claim is:

1. A method for obtaining a compound having antitumor activity from pig intestinal mucosa comprising:
   fractionating waste intestinal mass;
   extracting with acetic acid;
   precipitating with ethyl alcohol;
   ultrafiltration in the range of about 1 to about 6 kDa; and
   lyophilization of the ultrafiltrate,
   the method effective for isolating the antitumor compound which is an inhibitory enterocytogenin-2 (IEG$_2$) peptide having an amino acid sequence of SEQ. ID. NO.:1 bound to one guanine residue.

2. An IEG2 compound having antitumor activity obtained according to claim 1, wherein the IEG2 compound is a hexapeptide having an amino acid sequence of SEQ. ID. NO:1 bound to one guanine residue.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Other
      (B) LOCATION: 6...6
      (D) OTHER INFORMATION: C-terminal -NH2 group (xi) SEQUENCE DESCRIPTION: SEQ ID NO:1:

Arg Arg Asp Asp His Arg
1             5